US008865778B2

(12) United States Patent
Cao et al.

(10) Patent No.: US 8,865,778 B2
(45) Date of Patent: Oct. 21, 2014

(54) EXTENDED RELEASE EXCIPIENT AND ITS USE

(75) Inventors: Linqiu Cao, Wageningen (NL); John Richard Langridge, Sint Oedenrode (NL); Alexander Wilhelmus Van Gessel, Göttingen (DE)

(73) Assignee: Campina Nederland Holding B.V., Zaltbommel (NL)

( * ) Notice: Subject to any disclaimer, the term of this patent is extended or adjusted under 35 U.S.C. 154(b) by 750 days.

(21) Appl. No.: 12/519,034

(22) PCT Filed: Dec. 4, 2007

(86) PCT No.: PCT/NL2007/050620
§ 371 (c)(1),
(2), (4) Date: Sep. 4, 2009

(87) PCT Pub. No.: WO2008/072960
PCT Pub. Date: Jun. 19, 2008

(65) Prior Publication Data
US 2010/0087549 A1    Apr. 8, 2010

Related U.S. Application Data

(60) Provisional application No. 60/874,945, filed on Dec. 15, 2006.

(30) Foreign Application Priority Data

Dec. 15, 2006   (EP) .................................. 06126206

(51) Int. Cl.
A01N 25/00 (2006.01)
A61K 47/00 (2006.01)
A01N 25/34 (2006.01)
A61K 9/22 (2006.01)
A61K 9/20 (2006.01)

(52) U.S. Cl.
CPC ............ *A61K 9/2054* (2013.01); *A61K 9/2059* (2013.01)
USPC ............ 514/778; 514/781; 424/468; 424/408

(58) Field of Classification Search
USPC ........................ 514/778, 781; 424/468, 408
See application file for complete search history.

(56) References Cited

U.S. PATENT DOCUMENTS

| 6,476,006 B2 | 11/2002 | Flashner-Barak et al. |
| 6,500,459 B1 | 12/2002 | Chhabra et al. |
| 2009/0099154 A1 | 4/2009 | Jain et al. |
| 2009/0175941 A1 | 7/2009 | Francas |

FOREIGN PATENT DOCUMENTS

| CN | 101141962 A | 3/2008 |
| EP | 1 382 331 | 1/2004 |
| FR | 2 845 914 | 4/2004 |
| JP | 996283146 A | 10/1996 |
| JP | 2004501186 A | 1/2004 |
| JP | 2009500318 A | 1/2009 |
| WO | 97/46592 | 12/1997 |
| WO | 02/00204 | 1/2002 |
| WO | 02/070021 | 9/2002 |
| WO | 2004/006904 | 1/2004 |
| WO | 2004066981 | 8/2004 |
| WO | 2005/074976 | 8/2005 |
| WO | 2006066399 A1 | 6/2006 |

OTHER PUBLICATIONS

DE 19622790—English Machine Translation p. 1-5, 1997.*
WO 9746592 English Machine Translation p. 1-14, 1997.*
International Search Report dated Feb. 6, 2008, from corresponding PCT application.
M. Rahmouni et al., "Characterization of binary mixtures consisting of cross-linked high amylose starch and hydroxypropylmethylcellulose used in the preparation of controlled release tablets", Pharm. Dev. Technol. 4 (2003), pp. 335-348 (abstract only).
Raina et al., "Some Characteristics of Acetylated, Cross-linked and Dual-Modified Indian rice Starches", Eur. Food Res. Technol., 2006, vol. 223, pp. 561-570.

* cited by examiner

*Primary Examiner* — Uma Ramachandran
(74) *Attorney, Agent, or Firm* — Young & Thompson

(57) ABSTRACT

A controlled release excipient composition suitable in formulation of a slow or extended release tablet, contains a synergistic mixture of substantially uncross-linked carboxymethyl starch, or sodium starch glycolate (SSG), and a hydrophilic, non-ionic cellulose ether, preferably hydroxypropylmethylcellulose. Whether or not a SSG in the mixture is sufficiently uncross-linked in the context of the invention can be determined by sedimentation: 0.25 g of the formulation in 100 ml deionized water after 24 hours at 25° C., if subjected to centrifugation at 6080 G at 25° C. for 15 minutes, should exhibit a sedimentation volume of more than 60 ml.

16 Claims, No Drawings

EXTENDED RELEASE EXCIPIENT AND ITS USE

FIELD OF THE INVENTION

The invention pertains to an excipient composition suitable in formulation of a slow or extended release tablet with an active ingredient. The invention also pertains to substantially uncross-linked SSG for use in such an excipient composition.

BACKGROUND OF THE INVENTION

Polysaccharides and their derivatives are widely used in pharmaceutical formulations and, in several cases, they play a fundamental role in determining the release rate from the dosage form. This is desired in those cases where active ingredients only exhibit a small absorption window in the gastrointestinal tract or where a pharmaceutical composition is to be released in the body at a constant rate in a desired time scale.

Rahmouni et al. "*Characterization of binary mixtures consisting of cross-linked high amylose starch and hydroxypropylmethylcellulose used in the preparation of controlled release tablets*" Pharm. Dev. Technol. 4 (2003), pp. 335-348 mentions that cross-linked native high amylose starch has attracted a lot of attention as a controlled release excipient for the preparation of solid dosage forms. This is attributed to the swelling and gel-forming properties of the cross-linked starch matrix controlling the diffusion rate of the drugs.

The same article also reports that hydroxypropylmethylcellulose (HPMC) is a widely used hydrophilic polymer for the preparation of controlled release tablets. For that purpose, Rahmouni et al. evaluate the effect of a binary mixture of HPMC and cross-linked starch on tableting properties and the release kinetics of drugs of different solubilities. The outcome of the study is multiple, but in terms of release rate it was found that the incorporation of 10% HPMC reduces the release rate of poorly and moderately water-soluble drugs, while the release rate of highly water-soluble drugs was rapid both in the presence or absence of HPMC.

EP-A-1.382.331 discloses a pharmaceutical formulation designed for controlled release of active ingredients, wherein the tablet consists of multiple layers, i.e. a layer consisting of erodible and/or gellable and/or swellable hydrophilic polymers and a layer containing the active ingredient to be administered. The first layer acts as a barrier for drug release control, and may include HPMC or carboxymethylcellulose, among various other polymeric substances. In order to arrive at a swellable layer EP-A-1.382.331 exemplifies the use of AcDiSol (FMC Corp. Philadelphia, USA) and Explotab® (Mendel, Carmel, N.Y., USA), which are commercially available as cross-linked sodium carboxymethylcellulose (or croscarmellose sodium) and cross-linked sodium carboxymethyl starch (or sodium starch glycolate) respectively having moderate swelling potential.

WO-A-02/00204 and WO-A-02/070021 provide oral dosage forms for administering antineoplastic agents, where gelling of the gastric retention vehicle composition retain the antineoplastic drug in the patient's stomach. A superdisintegrant such as cross-linked carboxymethyl cellulose sodium, sodium starch glycolate or cross-linked polyvinyl pyrollidone may be used. Again, the SSG is cross-linked, given the fact that it is suggested to use Primojel® or Explotab®.

U.S. Pat. No. 6,500,459 describes a pharmaceutical composition for controlled onset and sustained release of an active ingredient, said composition comprising a hydrophilic carrier and a hydrodynamic diffusion enhancer. According to its examples, a mixture of HPMC and Explotab® SSG may be used.

WO-A-2004/066981 relates to an oral controlled release pharmaceutical composition comprising metaxalone. It may involve sodium starch glycolate as is commercially available as Explotab® and Primojel®.

WO-A-2004/006904 discloses oral controlled-release dosage forms containing acetaminophen. A list of disintegrants is given, among which Primojel® SSG.

Although some of the foregoing publications do not explicitly mention the SSG to be highly cross-linked, the suggested use of Primojel® or Explotab® inevitably implies that it is highly cross-linked SSG that is strived for in the art. Both Primojel® and Explotab® are used as a reference in the accompanying examples, supporting the invention. WO-A-97/46592 teaches the use of a substantially uncross-linked carboxymethyl starch as an auxiliary agent for retarding drugs release. Although measures are taken to prevent cross-linking during etherification of native starch and subsequent drying, the carboxymethyl starch of WO-A-97/46592 still involves cross-linking to a reasonable extent, due to intermolecular esterification between the carboxyl moieties of carboxymethyl substituents and the remaining hydroxyl moieties of carboxymethyl starch. WO-A-97/46592 does not mention the actual amount of cross-linking. Moreover, the international publication is silent on the slow release properties of the carboxymethyl starch in combination with other excipients.

Outside the field of slow release tableted drugs, cross-linked carboxymethyl starch is widely known for its remarkable efficiency in tablet disintegration and enhanced dissolution of the tablet, and is often incorporated in tablet formulations where accelerated absorption of water is needed to disintegrate the tablet as fast as possible; the function of this type of cross-linked carboxymethyl starch is not to retard drug release.

However, neither the reported controlled release excipients HPMC and carboxymethyl starch, to some extent cross-linked, nor the combination of HPMC and cross-linked carboxymethyl starch give satisfactory slow drug release. Hence, in the art there is a continuous need to further improve the slow release properties of tableted drugs through the choice of excipient(s).

SUMMARY OF THE INVENTION

It is an object of the invention to provide a rate-controlling excipient which enables improved control over active ingredient release from tablets when compared to the individual conventional rate-controlling excipients, and without otherwise compromising the tablet properties. It is especially an objective to provide an excipient for slow or extended release.

It is now found that a combination of carboxymethyl starch and a hydrophilic, non-ionic cellulose ether has a synergistic effect on active ingredient release rates, provided that the carboxymethyl starch is substantially uncross-linked.

The surprising effect is evidenced in the accompanying examples by means of sedimentation measurements, which are demonstrated to be directly linked to the release rate of the active ingredient in an aqueous system. Although not wishing to be bound by any theory, it is the inventors' belief that the interaction of the cellulose ether with the substantially uncross-linked carboxymethyl starch leads to the formation of a stronger dissolution rate controlling matrix structure than can be obtained using the individual components.

The dissolution rate controlling matrix behaves as follows. Water or gastrointestinal fluid first hydrates the polymers at the surface of the tablet and the hydrated polymers form a viscous gelled outer layer to the tablet. This layer contains not only the polymers but also all the other formulation components including the active ingredient. This outer layer serves two functions: first it reduces the rate of water ingress into the core of the tablet, and secondly it controls the rate at which active ingredients diffuse out of the layer and into the surrounding liquid. The outer gelled layer is slowly dissolved or otherwise eroded, but a new hydrated and gelled layer is constantly formed deeper within the tablet. The overall effect is that the tablet slowly dissolves away as the hydrated and gelled layer moves inward towards the core of the tablet, and the outer layers dissolve. Thus, improving the dissolution rate of the tablet implies modulation of the gel strength by selecting appropriate gel-forming excipients.

In the invention it is essential that the carboxymethyl starch is substantially uncross-linked. The slow release properties are found to deteriorate with an increasing degree of cross-linking, since a high degree of cross-linking in the carboxymethyl starch promotes the actual fast gel dissolution instead of controlled slow release.

DESCRIPTION OF THE INVENTION

The invention thus pertains to a rate-controlling excipient composition containing a substantially uncross-linked carboxymethyl starch and a hydrophilic, non-ionic cellulose ether. The composition enables slow or extended release of the active ingredient contained in the tablet formulation.

Although the term "active ingredient" is predominantly understood to comprise drugs in pharmaceutical sense, it also encompasses nutritional ingredients like vitamins, minerals, proteins, peptides, enzymes, micro-organisms, flavours etc.
Hydrophilic Non-Ionic Cellulose Ether In principle, the cellulose ether in the excipient composition may be in any form, provided it is hydrophilic and satisfies the criteria set below.

In general, the cellulose ether is selected from alkyl celluloses, hydroxyalkyl celluloses and hydroxyalkyl alkyl celluloses. The cellulose ethers may contain some further substitution with other non-ionic groups, such as acyl groups from esters e.g. acetate and propionate substituents. Examples of suitable cellulose ethers are methylcellulose (MC), ethylcellulose (EC), hydroxyethyl cellulose (HEC), hydroxypropyl cellulose (HPC), hydroxypropyl methylcellulose (HPMC), hydroxypropyl ethylcellulose (HPEC), ethylhydroxyethylcellulose (EHEC), hydroxyethyl methylcellulose (HEMC), and the like.

More preferably, the cellulose ether is one which is listed in the major national or multinational Pharmacopoeias, such as MC, HEC, CMC or HPMC. For example, hydroxypropylmethylcellulose appears in the European Pharmacopoeia, The United States Pharmacopoeia and the Japanese Pharmacopoeia.

The nature and quantity of substituent groups attached to the anhydroglucose ring of the cellulose ether are factors which influence properties such as organic solubility and the thermal gelation temperature of aqueous solutions containing the cellulose ether. It is within the ambit of the skilled person's knowledge to determine the actual degree of substitution and the molecular weight of the selected cellulose ether suitable for the controlled release application.

The viscosity of the cellulose ether also affects texture and the strength of the gel. It is generally accepted that drug dissolution from tablets is slower for higher molecular weights cellulosics. Usually, the gel strength may level off at molecular weights greater than approximately 150,000. The molecular weight of the cellulose ether is preferably in the range of 4,000-100,000. However, for drugs having a relatively low water-solubility, combinations of cellulose ethers including those having lower viscosity grades may be used.

In the most preferred embodiment, the cellulose ether is HPMC, typically the polymer of choice for a rate-controlling carrier in existing hydrophilic matrix systems for extended active ingredient release. Its popularity may be attributed to its safety, availability, global compliance and physicochemical/mechanical characteristics. In addition, it is belief in the art that HPMC encourages gel formation which is much stronger and tighter compared to other cellulosics. Mixtures of HPMC with other cellulose ethers, e.g. in a weight ratio of 99:1 to 1:1 can also be used. However, it is preferred that HPMC is the predominant cellulose ether in the mixture.

HPMC is a linear cellulose polymer comprising etherified anhydroglucose rings, prepared by treating cellulose fibers with caustic solution, which in turn is treated with methyl chloride and propylene oxide. In the art, HPMC is considered a amphiphilic polymer, which solution properties are defined by the average number of methoxyl and hydroxypropyl substituents per glucose unit. In the field, DS and MS are used to express the average methoxyl and hydroxypropyl degree of substitution. DS is a measure of the hydrophobic properties, while MS is a measure for the hydrophilicity of the polymer.

In principle the invention is not limited to a particular source of HPMC. A suitable HPMC candidate is characterized by a DS of about 0.1-0.5 and an MS of about 1.0-3.0, thus being characterized by a predominantly hydrophilic nature. It is preferred that the total molar substitution is at least 1.0, preferably at least 2.0, most preferably at least 2.5. Alternatively, in terms of weight percentages, it is preferred that the HPMC of the invention contains 15-35 wt % methoxy groups and 2-15 wt % hydroxypropyl units. HPMC may be used as commercially available controlled-release substituted cellulosics, for example as Methocel E, F or K from Dow Chemicals. Good results are for example obtained for HPMC K 15 M or HPMC-HM 15000 PA2208 as commercially available from Wolff Cellulosics, Germany).
Uncross-Linked Carboxymethyl Starch The term "carboxymethyl starch" is considered being synonymous with the terms "starch ether" and "starch glycolate". Throughout the description and claims, together with its associated sodium counter-ion, it is conveniently abbreviated as SSG.

SSG is typically prepared from native starch with sodium monochloroacetate or monochloracetic acid in alcohol under alkaline conditions. Good examples of cross-linked SSGs are Primojel®, commercially available with DMV International (Veghel, The Netherlands), and Explotab® (Mendel, Carmel, N.Y., USA/JRS Pharma, Germany).

However, unlike the aforementioned SSGs on the market today, the sodium carboxymethyl starch or sodium starch glycolate used in the current invention is substantially uncross-linked and has a degree of substitution (SSG-DS) preferably in the range of 0.1-0.5. In one embodiment the SSG-DS is preferably between 0.22 and 0.32, since these values are in compliance with the standards of the Pharmacopoeia. It is shown in the accompanying examples 4 and 5 (tables 3 and 4) that Primojel® and Explotab® are unsuitable for this purpose.

However, it is found that best results in terms of synergy are found in cases where SSG-DS is high. Hence, in a preferred embodiment the carboxymethyl starch has a SSG-DS of 0.28-0.4. In theory, SSG-DS may in fact still be higher, but difficulties arise in the preparation process, where a high SSG-DS leads to a very high viscous reaction mixture and is therefore difficult to prepare on industrial levels. However, the skilled person should be aware that this limitation might be circumvented by optimising the reaction techniques for example by changing the reaction temperature, or ethanol/water ratio and volume in the reaction mixture.

In contrast to the cellulose ether applied in the present invention, SSG is a charged polymer. Furthermore, SSG is completely hydrophilic by nature. However, since SSG may be synthesized in a water-miscible organic solvent, such as ethanol, methanol and isopropanol, the SSG surface may contain some hydrophobic structural moieties, due to the three-dimensional folding of the molecules. Therefore, the interaction between the cellulose ether and SSG may not be limited to hydrogen bonding, but may also include hydrophobic interactions. Especially when the dried mixture of cellulose ether/SSG is exposed to an aqueous medium, the hydrophobic interaction might be dominant. The surface-exposed hydrophobic groups in SSG might initially endow the interaction of the cellulose ether molecules with SSGs more hydrophobic nature, while the hydrophilic interactions might gradually become more dominant as dissolution of the cellulose ether and SSG progresses. As a result, different dissolution rates may be observed for mixtures formed from different SSGs, most probably related to their actual production process. However, the same synergistic trends return in all SSGs tested, all within the desired range of the invention. It is found that best results are obtained when the synthesis involves an ethanol/water mixture having a weight ratio of between 4:1 and 6:1.

As aforementioned, the SSG of the invention is substantially uncross-linked. Unfortunately, in practice the actual amount of cross-linking in SSG is hard to determine directly. Hence, "substantially uncross-linked" is meant to comprise SSG which preparation route involves little or no cross-linking. However, optimum results are obtained with a small degree of cross-linking, in the context of the invention this is considered to be comprised in the term "substantially uncross-linked". An excellent test method to evaluate the suitability of an SSG in the context of the invention is to determine its sedimentation volume, which is clearly linked to the dissolution rate of active ingredient from the tablet. The accompanying examples serve as evidence thereof.

A substantially uncross-linked SSG in accordance with the present invention is characterized by a high sedimentation volume or gel volume: The sedimentation volume increases with a decreasing degree of cross-linking. If 0.25 g of SSG is dissolved or dispersed in 100 ml deionized water at 25° C., its sedimentation volume after 24 hours should be higher than 85 ml, preferably higher than 90 ml. For sake of reference, completely uncross-linked SSG would exhibit a maximum sedimentation volume of 100 ml, while highly cross-linked SSG, as it is conventionally used as a disintegrant, exhibit a sedimentation volume of about 9-15 ml. However, since cellulose ethers may interfere with the test results, the above test only applies to "pure" SSG, meaning that the SSG is not polluted by the presence of any cellulose ether material. This test will be referred to hereafter as the "first sedimentation volume test".

To determine the suitability of a carboxymethyl starch in a mixture with a cellulose ether, such as HPMC, the first sedimentation volume test is extended with an additional step of centrifugation: 0.25 g of the mixture is sampled and dissolved or dispersed in 100 ml deionized water. After 24 hours of sedimentation at 25° C., the sample is centrifuged at 6080 G at 25° C. for 15 minutes. The upper (ungelled) layer is decanted, the remainder forming the sedimentation volume or gel volume. A substantially uncross-linked carboxymethyl starch in a mixture with a cellulose ether exhibits a sedimentation volume of more than 60 ml, preferably even more than 80 ml. Repeating the foregoing test, with only substantially uncross-linked carboxymethyl starch shows a value of 100 ml. In the examples it is shown that a cross-linked and thus unsuitable carboxymethyl starch would at most give a sedimentation volume of about 50 ml, at a carboxymethyl starch: cellulose ether ratio of 1:1. More carboxymethyl starch would reduce the sedimentation volume, while no carboxymethyl starch (only cellulose ether) would give a sedimentation volume of zero. Although 100% HPMC (in absence of any SSG) would also result in a sedimentation volume of 100 ml pursuant the foregoing test conditions, one can easily distinguish pure 100% HPMC from the synergistic HPMC/SSG mixtures according to the invention, for instance by performing a colouring method such as the Lugol test.

The SSG preparation also involves a drying step. However, drying is considered to involve some kind of a dehydration, which often provokes the formation of physical cross-links. Chemical cross-linking between hydroxyl and carboxyl groups in the SSG may also occur, especially at low pH. In order to prevent the formation of uncontrolled cross-links, care should be taken to control the drying step. The skilled person should be aware that the best drying method, which might be implementable in the production, can be determined experimentally.

The source of starch is not considered to be a limiting factor. However, it is preferred to use a sodium carboxymethyl starch prepared from potato starch, since it has been shown in the past to be more effective in tablet disintegration than SSG prepared from maize, waxy maize, wheat, rice or tapioca starch. The starch may also be pre-gelatinized, since retention of its grain structure is not a requisite for its use in excipient formulations according to some Pharmacopoeial Monographs. The molecular weight of the carboxymethylated starch is determined by its source, but may be estimated between 100,000-50,000,000.

The SSG is preferably no longer crystalline, since its preparation involves the use of strong alkaline conditions, and its purification involves water addition and flash drying, all of which destroy the crystallinity of the starch grains to a large extent.

Synergistic Mixture

In order to arrive at the synergistic effect of the excipient of the invention, the cellulose ether and the carboxymethyl starch may be combined with the active ingredient(s) in a slow or extended release tablet using tableting techniques known in the art, such as direct compression, dry and wet granulation technologies, including, but not limited to, low-shear, high-shear and fluid bed processes. The release of the active ingredient is not influenced by the method of tablet manufacture using the hydrophilic matrix mixture of the invention; neither is it affected by the hydrophilic/hydrophobic nature of the active ingredient itself.

The cellulose ether, preferably HPMC, and the SSG are present in the synergistic excipient in a weight ratio between 9:1 and 1:3, preferably in the range of 7:1 to 1:2. Best results are obtained for weight ratios lower than 4:1, most preferably lower than 3:1, in particular lower than 2:1, in particular 1:1 or less.

It is preferred that the mixture of the cellulose ether and SSG is homogeneous, e.g. achieved by blending. This enables full interaction between the combined excipients once it comes into contact with water.

The invention also relates to a slow or extended release tablet containing the above-discussed excipient ratios and one or more active ingredients. The tableted composition preferably contains the excipient combination in an amount of 10-60 wt %, more preferably at least 20 wt %, based on the total weight of the tablet. The tableted composition preferably contains 30-50 wt % excipient combination. It is found that a high percentage of the polymeric mix, especially in combination with a HPMC:SSG weight ratio in the range of 2:1-1:2, is favoured for a long slow or extended release profile. Therein, it is observed that the drug-release profile in a mixture of SSG/HPMC within the aforementioned ranges is more responsive to changes in the HPMC concentration than for HPMC alone. It is, however, recommended that the actual proportion to be included in each individual formulation is determined experimentally.

The invention further pertains to the use of the aforementioned combination of cellulose ether, in particular HPMC, and SSG in controlled release formulations. While the focus is on the release of pharmaceutical agents, either hydrophilic or hydrophobic, the combination of the invention may also be applied in the controlled release of nutritional ingredients or nutraceuticals.

The invention further pertains to the use of substantially uncross-linked SSG in a controlled release formulation, as described above. With substantially uncross-linked SSG it is understood SSG which yields a sedimentation volume of more than 85 ml, preferably more than 90 ml, in the foregoing first sedimentation volume test.

EXAMPLES

Example 1

Preparation of Cross-Linked and Uncross-Linked SSG (a) Reaction Conditions 120 gram native non-cross-linked potato starch (Solani Amylum from Avebe, the Netherlands) or equivalent amount of cross-linked potato starch, which was prepared according to the method reported in the literature [Yoneya et al., "*Influence of cross-linked potato starch treated with POCl$_3$ on DSC, rheological properties and granule size*"; Carbohydrate Polymer 2003, 55:447-457] was dispersed in 380 g of 90% ethanol, then 17.5 gram of demineralised water, 17.5 gram of SMCA (sodium monocholoroacetate) and 7.5 g of sodium hydroxide pellet were added with stirring. The reaction mixture was warmed to 70° C. with stirring within 30 minutes. The reaction mixture was further stirred at 70° C. for 6 hours. Subsequently, the reaction mixture was cooled to 50° C., and, 47 gram of 3.3% HCl in 90% ethanol was added slowly to neutralise the remaining NaOH in the reaction mixture. The pH of the final product was controlled in the range of pH 5.5-7.0.

(b) Purification of SSGs

After filtration of the neutralised suspension using a Büchner funnel, the obtained SSG cake was dispersed in 380 gram 90% ethanol, stirred at 45° C. for 15 minutes and the suspension was filtered using a Büchner funnel. The above washing and filtration process was repeated. The final cake product was dried using a fluid bed drier for 10 minutes at 60° C. prior to use.

The SSG prepared as above has a degree of substitution (DS) of about 0.2. Other SSGs with 0.3 and 0.4 were prepared under the same conditions by simply varying the amount of SMCA and NaOH in proportion.

Example 2

Relationship Between DS and Dissolution Rate of SSG in HPMC/SSG Mix (a) Formulation of Tablets Containing HPMC/SSG Mix In order to test the effect of DS of the SSGs (prepared as in example 1) on active ingredient dissolution rate, tablets containing HPMC/SSGs were made using the following formulation, to form three sets of tablets with variation in the degree of substitution of the sodium starch glycolate (DS=0.2/0.3/0.4):

- 20% metoprolol tartrate (active ingredient) (Fagron, Germany);
- 39% lactose (DCL14 from DMV-Fonterra Excipients, Germany);
- 20% HPMC-W, namely hydroxypropylmethylcellulose (Walocel HM 15.000 PA 2208 from Wolff Cellulosics, Germany);
- 20% substantially uncross-linked sodium starch glycolate with different degrees of substitution (DS=0.2, 0.3 and 0.4) prepared according to Example 1;
- 0.5% colloidal silica (Aerosil 200 from Degussa); and
- 0.5% magnesium stearate (BUFA, the Netherlands).

These components were dry blended to give a homogenous mixture. The formulation quantities are expressed in weight percentages of the total mixture.

(b) Formulation of the Reference Tablets

As a reference the above formulation was also prepared with the aforementioned components and amounts thereof, except that the mixture of 20% HPMC-W and 20% SSG was now replaced by 40% HPMC-W (Walocel HM 15000 PA 2208 from Wolff Cellulosics, Germany).

(c) Preparations of Tablets

The dry mixtures were compressed to produce 250 mg tablets at a compression force of 10 kN using a Korsch EKO eccentric press equipped with round flat beveled punches with a diameter of 9 mm. Tablets were made individually by weighing 250 mg of powder mixture before placing the material in the die.

(d) Dissolution Experiments

In order to determine the release profile of the tablets, dissolution testing was performed in 900 mL of deionised water using USP apparatus 2 stirred at 50 rpm. To follow the release profile of metoprolol tartrate, UV-spectrometry at a wavelength of 222 nm was used to analyze samples taken periodically from the dissolution medium. The drug release (dissolution) profile of the tablet containing metoprolol tartrate is given as percentage of the target drug content released over time.

The average results of six tablets are shown in Table 1, together with those obtained for 40% SSG (DS 0.3; results taken from table 5). These data show that the formulations of 20% HPMC/20% SSGs of different DS (0.2, 0.3 and 0.4) all give improved controlled release profile, compared with the reference formulations with only 40% HPMC and 40% SSG. The tablets formulated by the present invention exhibit substantially slower or extended drug release than the reference tablets.

TABLE 1

Dissolution of tablets over time

Percentage drug released (%)

| Time (min) | HPMC-W + SSG with DS = 0.2 | HPMC-W + SSG with DS = 0.3 | HPMC-W + SSG with DS = 0.4 | 40% HPMC-W (reference) | 40% SSG with DS = 0.3 (reference) |
|---|---|---|---|---|---|
| 0 | 0 | 0 | 0 | 0 | 0 |
| 5 | 3.4 | 2.2 | 3.2 | 4.3 | 2.4 |
| 15 | 8.6 | 6.2 | 6.9 | 9.8 | |
| 30 | 14.8 | 10.8 | 12.2 | 16.1 | 18.8 |
| 60 | 22.9 | 17.8 | 18.1 | 26.8 | 38.4 |
| 90 | 27.7 | 23.4 | 23.3 | 35.1 | 55.3 |
| 120 | 32.8 | 28.1 | 28.6 | 41.7 | |
| 180 | 40.3 | 36.3 | 37.0 | 52.3 | 88.2 |
| 240 | 48.0 | 43.4 | 45.1 | 60.7 | 95.9 |
| 300 | 53.1 | 50.2 | 52.7 | 67.4 | |
| 360 | 58.8 | 56.3 | 59.8 | 73.0 | |
| 420 | 64.1 | 62.5 | 66.9 | 77.7 | |

Similar results were obtained for the dissolution profile of theophylline, which has a pH-dependent solubility in water, instead of the lipophililic drug metoprolol tartrate used above.

Example 3

Effect of Cross-Linking Degree of SSG on Drug Release Profile (a) Preparation of Cross-Linked SSGs with Different Cross-Linking Degree SSGs with different cross-linking degree were prepared according to the methods described in example 1. The degree of cross-linking (XL, %) in the specified SSG was defined as follows:

$$XL(\%) = (CL/CL_{max}) * 100\%$$

Here, CL represents the amount of cross-linking agent used in the preparation of the corresponding SSG, while $CL_{max} = 0.3\%$ (based on the weight amount of starch) is the amount of cross-linker $POCl_3$ which is traditionally used for preparing highly cross-linked SSG suitable as a disintegrant [see Yoneya et al., "*Influence of* cross-linked potato *starch* treated with $POCl_3$ on DSC, rheological properties and granule size*"*; Carbohydrate Polymer 2003, 55:447-457]. Such a cross-linked SSG disintegrant exhibits a sedimentation volume of about 9-15 ml, as measured with the method described in example 4(a). The variation may be due to the type of cross-linking agent, in this particular case $POCl_3$.

(b) Formulation of Tablets Containing SSGs of Different Cross-Linking Degree

To investigate the effect of cross-linking of the SSGs on the dissolution profile tablets were made using the following formulation to form six sets of tablets with variation in the degree of cross-linking of the sodium starch glycolate (XL=0%, 4.8%, 9.6%, 14.6%, 36.5% and 100%). Sodium starch glycolate with 100%-XL is an equivalent of the one under study in the aforementioned publication by Yoneya et al.

Uniform dry blends were prepared from:
20% metoprolol tartrate (Fagron, Germany);
49% lactose (DCL14 from DMV-Fonterra Excipients, Germany);
15% HPMC-W (Walocel HM 4.000 PA 2208 (Wolff Cellulosics (DE)));
15% substantially uncross-linked sodium starch glycolate with a degree of substitution of 0.3 prepared according to Example 1;
0.5% colloidal silica (Aerosil 200 from Degussa, Germany); and
0.5% magnesium stearate (BUFA, the Netherlands).

As a reference the same ingredients and amounts thereof were used, wherein the mix of 15% HPMC and 15% SSG were replaced by 30% HPMC-W (Walocel HM 4.000 PA 2208).

(c) Preparation, Dissolution and Analysis

Preparation and analysis of tablets were performed according to the procedure mentioned in examples 2c and 2d. The average dissolution results with six different formulated tablets were tabulated in Table 2.

Table 2 shows excellent dissolution with the combined polymeric mix is obtained with SSGs which are substantially uncross-linked. Increasing the degree of cross-linking lowers the synergy to a point where the combination no longer improves dissolution.

TABLE 2

Dissolution of tablets over time

Percentage drug released (%)

| Time (min) | HPMC/ SSG with XL = 0% | HPMC/ SSG with XL = 4.8% | HPMC/ SSG with XL = 9.6% | HPMC/ SSG with XL = 14.6% | HPMC/ SSG with XL = 36.5% | HPMC/ SSG with XL = 100% |
|---|---|---|---|---|---|---|
| 0 | 0 | 0 | 0 | 0 | 0 | 0 |
| 5 | 8.9 | 10.7 | 8.7 | 26.8 | 37.8 | 17.4 |
| 10 | | | 11.7 | | | 25.3 |
| 15 | 17.6 | 13.3 | 14.3 | 62.7 | 92.2 | 29.6 |
| 30 | 25.2 | 15.4 | 20.7 | 78.3 | 93.2 | 38.8 |
| 60 | 35.8 | 21.3 | 30.1 | 86.6 | 93.8 | 58.3 |
| 90 | 43.6 | 31.1 | | 89.9 | 94.1 | |
| 120 | 50.1 | 44.3 | 45.4 | 92.5 | 94.8 | 75.5 |
| 180 | 61.7 | 55.8 | 58.3 | 96.0 | 95.9 | 84.8 |
| 240 | 70.4 | 65.3 | 70.2 | 97.6 | 99.8 | 89.1 |
| 300 | 79.0 | 74.0 | 80.3 | 98.7 | 101.2 | 93.0 |
| 360 | 86.1 | 81.6 | 88.7 | 99.3 | | 93.8 |
| 420 | 92.5 | 88.5 | 95.7 | | | 94.7 |

Example 4

Relationship of Sedimentation, Dissolution and Cross-Linkage of SSG Alone (a) Determination of Sedimentation Volume of SSG Alone The sedimentation volume of tablets containing SSGs with different degrees of cross-linking was determined according to the following method: 0.25 g of each corresponding SSG was mixed in a 100 ml measuring cylinder with 100 mL of deionised water and measured after standing for 24 hours. Sedimentation volume corresponds to gel formation as visible by the eye.

(b) Determination of $t_{50\%}$ $t_{50\%}$ is defined as the time point at which 50% of the active ingredient is released from the tablet formulated with the corresponding SSG. Thus, $t_{50\%}$ was interpolated from the data given in example 3(c).

The relationship of the sedimentation volume of SSGs and $t_{50\%}$ of the formulations containing the corresponding SSG is tabulated in Table 3. Therein, a sedimentation volume of 100 ml means that no measurable phase separation is observed (the SSG is dissolved or dispersed completely over the whole continuum measuring volume (100 ml).

TABLE 3

Influence of cross-linking of SSGs on sedimentation volume and $t_{50\%}$

| Degree of cross-linking (%) | Sedimentation volume (ml) | Time for 50% of active drug to be released (min) |
| --- | --- | --- |
| 0 | 100* | 120 |
| 4.8 | 100* | 150 |
| 9.6 | 100* | 140 |
| 14.6 | 81 | 11 |
| 36.5 | 59 | 7.5 |
| 100 | 11 | 44 |

*No measurable phase separation (the SSG is dissolved or dispersed completely over the whole continuum measuring volume (100 ml)

As shown in Table 3, the sedimentation volume of cross-linked SSG decreases with increasing cross-linking degree. Slow or extended release performance was dramatically increased when the SSG has XL=14.6% or lower and a sedimentation volume greater than 81 ml.

Example 5

Relationship of Sedimentation, Dissolution and Cross-Linkage of SSG/HPMC

The sedimentation test of example 4(a) was repeated, but now sedimentation volume was determined for SSG having XL=18.5%, SSG having XL=12.9%, and SSG having XL=0%, in the presence of different amounts of HPMC, including a reference containing no HPMC. For reference, the effects of XL=100% SSG without and in combination with HPMC were also demonstrated, using the commercially available Primojel® and Explotab® as the source of SSG.

In order to achieve this, the sedimentation volume of powder mixtures containing SSGs and HPMC was determined according to the following method: 0.25 g of SSG and a variable amount of HPMC was mixed in a 100 ml measuring cylinder with 100 mL of deionised water. After 24 hours the aqueous mixture was centrifuged at 6000 rpm and 6080 G at 25° C. for 15 minutes. The upper layer was decanted if visible. The volume of the gel remaining in the centrifuge tube was the sedimentation volume.

For sake of completeness, table 4 also encompasses the recalculated sedimentation volume values if the total sample weight was 0.25 g. These calculations were confirmed experimentally. The cross-linked values in Table 4 are relative to a value of 100% assigned to highly cross-linked Explotab/Primojel.

TABLE 4 sedimentation volume in the presence or absence of HPMC

| SSG-type | SSG (g) | HPMC (g) | Sedimentation volume (ml, 24 hour) | Sedimentation volume (ml; after centrifugation) | Sedimentation volume (recalculated; 0.25 g sample) |
| --- | --- | --- | --- | --- | --- |
| Explotab ® (XL = 100%) | 0.25 | 0 | 11 | 9 | 9 |
| Explotab ® | 0.25 | 0.25 | 11 | 9 | 4.5 |
| Explotab ® | 0.25 | 0.125 | 11 | 9 | 6 |
| Primojel ® (XL = 100%) | 0.25 | 0 | 11 | 9 | 9 |
| Primojel ® | 0.25 | 0.25 | 11 | 9 | 4.5 |
| Primojel ® | 0.25 | 0.125 | 11 | 9 | 9 |
| XL = 18.5% | 0.25 | 0 | 67 | 42.5 | 42.5 |
| XL = 18.5% | 0.25 | 0.25 | 99 | 49.1 | 24.6 |
| XL = 18.5% | 0.25 | 0.125 | 94 | 43.8 | 29.2 |
| XL = 12.9% | 0.25 | 0 | 97 | 100 | 100 |
| XL = 12.9% | 0.25 | 0.25 | 100 | 100 | 100 |
| XL = 0% | 0.25 | 0 | 100 | 100 | 100 |
| XL = 0% | 0.25 | 0.25 | 100 | 100 | 100 |

Example 6

Effect of SSG:HPMC Ratio (a) Formulation with Different SSG:HPMC Ratios Varying from 3:1 to 1:3

Five tablet formulations were prepared as follows:
20% Metoprolol tartrate (Fagron, Germany);
39% lactose (DCL14 from DMV-Fonterra Excipients, Germany);
0.5% colloidal silica (Aerosil 200 from Degussa, Germany);
0.5% magnesium stearate (BUFA, the Netherlands); and
40% total polymer, containing in different ratios:
  HPMC (Metolose 90H 4.000 2208 from ShinEtsu, Japan); and
  uncross-linked SSG (DS=0.3) prepared according to Example 1.

The ratios of HPMC and SSG studied were: 1:0, 3:1, 1:1, 1:3 and 0:1.

(b) Dissolution Test

Tablets were prepared from the above formulations and analyzed according to the procedure described in example 2(c) and 2(d). The averaged results of the dissolution of six tablets are shown in Table 5.

The data show that the composite excipients containing 40% HPMC-SE/SSG in ratios varying from 3:1 to 1:3 all show improved drug release profiles, compared to SSG or HPMC alone.

TABLE 5

Dissolution of tablets over time

| | | Percentage drug released | | | |
|---|---|---|---|---|---|
| Time (min) | SSG | SSG:HPMC-SE ratio 3:1 | SSG:HPMC-SE ratio 1:1 | SSG:HPMC-SE ratio 1:3 | HPMC-SE |
| 0 | 0 | 0 | 0 | 0 | 0 |
| 5 | 2.4 | 1.8 | 1.9 | 4.8 | 4.5 |
| 15 | | | 4.8 | 9.6 | 10.1 |
| 30 | 18.8 | 7.1 | 8.1 | 14.1 | 15.8 |
| 45 | | | | | 20.5 |
| 60 | 38.4 | 13.3 | 13.4 | 20.6 | 24.6 |
| 90 | 55.3 | 19.5 | 18.7 | 26.0 | 31.7 |
| 120 | | | 23.4 | 30.7 | 37.9 |
| 130 | 74.3 | 27.3 | | | |
| 150 | 80.1 | | | | |
| 180 | 88.2 | 37.3 | 31.0 | 38.7 | 48.1 |
| 210 | 93.0 | | | | |
| 240 | 95.9 | 49.7 | 39.5 | 45.3 | 59.7 |

Example 7

Dissolution Profile for Different Polymeric Contents (a) Formulation of Tablet Containing 30-40% Polymeric Excipient in Formulation The following tablet formulations were prepared:
20% metoprolol tartrate (Fagron, Germany);
59-39% lactose (DCL14 from DMV-Fonterra Excipients, Germany);
0.5% colloidal silica (Aerosil 200 from Degussa, Germany);
0.5% magnesium stearate (BUFA, the Netherlands); and
30-40% polymer
  HPMC (Metolose 90H 4.000 2208 from ShinEtsu, Japan); and
  uncross-linked SSG (DS=0.3) prepared according to Example 1.

The HPMC:SSG weight ratio was 1:1.
The results were compared with those for HPMC alone (weight ratio HPMC:SSG=1:0).

(b) Preparation, Dissolution and Analysis

Tablets were prepared and analyzed according to the procedure described in Example 2(c) and 2(d). The average results of the dissolution of six tablets are shown in Table 6.

The combination shows in both cases (with 30% and 40% total polymeric mix (HPMC:SSG=1:1) in the total formulation improved drug release profile, compared to that of HPMC itself at the same total percentage in the formulation.

TABLE 6

Dissolution of tablets over time

| | Percentage drug released (%) | | | |
|---|---|---|---|---|
| Time (min) | 30% HPMC | 30% HPMC/SSG 1:1 | 40% HPMC | 40% HPMC/SSG 1:1 |
| 0 | 0 | 0 | 0 | 0 |
| 5 | 3.5 | 2.6 | 4.5 | 1.9 |
| 15 | 9.6 | 6.6 | 10.1 | 4.8 |
| 30 | 17.1 | 11.8 | 15.8 | 8.1 |
| 45 | | | 20.5 | |
| 60 | 27.6 | 18.9 | 24.6 | 13.4 |
| 90 | 36.3 | 25.0 | 31.7 | 18.7 |
| 120 | 44.2 | 30.5 | 37.9 | 23.4 |
| 150 | 49.3 | | | |
| 180 | | 39.2 | 48.1 | 31.0 |
| 210 | 59.5 | | | |
| 240 | | 47.8 | 59.7 | 39.5 |
| 270 | 71.1 | | | |
| 300 | | 55.5 | 64.8 | 45.6 |
| 330 | 78.5 | | | |
| 360 | | 63.2 | 71.0 | 53.1 |
| 390 | 87.2 | | | |
| 420 | | 71.3 | 77.2 | 59.7 |
| 450 | 87.8 | | | |
| 480 | | 75.4 | 80.2 | 65.1 |

Example 8

Effect of HPMC with Different Viscosities (a) Formulation of Tablet Containing HPMCs with Different Viscosities To show that the mixture also displays the synergetic effect when using HPMC with a higher viscosity, the following formulation was used:
20% metoprolol tartrate (Fagron, Germany);
39% lactose (DCL14 from DMV-Fonterra Excipients, Germany);
20% HPMC-W, selected from:
  Walocel HM 4,000 PA 2208;
  Walocel HM 15,000 PA 2208 (both from Wolff Cellulosics, Germany);
20% un-cross-linked SSG (DS=0.3) prepared according to Example 1;
0.5% colloidal silica (Aerosil 200 from Degussa, Germany); and
0.5% magnesium stearate (BUFA, the Netherlands).

These components were blended to give a homogenous mixture.

As a reference the same formulation was prepared, without SSG but with 40% HPMC.

(b) Preparation, Dissolution and Analysis

Tablets were prepared and analyzed according to the procedure described in Example 2(c) and 2(d). The average results of the dissolution of six tablets are shown in Table 7.

TABLE 7

Dissolution of tablets over time

Percentage drug released (%)

| Time (min) | SSG with DS = 0.3/HPMC-W 4000 2208 | HPMC-W 4000 2208 | SSG with DS = 0.3/HPMC-W 15000 2208 | HPMC-W 15000 2208 |
|---|---|---|---|---|
| 0 | 0 | 0 | 0 | 0 |
| 5 | 2.6 | 5.0 | 2.2 | 4.3 |
| 15 | 6.8 | 10.7 | 6.2 | 9.8 |
| 30 | 11.9 | 17.3 | 10.8 | 16.1 |
| 60 | 19.8 | 28.1 | 17.8 | 26.8 |
| 90 | 26.1 | 36.8 | 23.4 | 35.1 |
| 120 | 31.9 | 43.8 | 28.1 | 41.7 |
| 180 | 41.9 | 55.1 | 36.3 | 52.3 |
| 240 | 51.0 | 64.2 | 43.4 | 60.7 |
| 300 | 59.6 | 71.0 | 50.2 | 67.4 |
| 360 | 67.8 | 77.1 | 56.3 | 73.0 |
| 420 | 75.2 | 81.6 | 62.5 | 77.7 |

The invention claimed is:

1. A slow or extended release excipient composition comprising: a substantially uncross-linked sodium starch glycolate (SSG), and hydroxypropylmethylcellulose (HPMC), wherein, the SSG has a degree of substitution in a range of 0.1-0.5, and wherein 0.25 g of said substantially uncross-linked SSG, when dissolved or dispersed in 100 ml deionized water at 25° C., exhibits a sedimentation volume after 24 hours greater than 85 ml, and the HPMC and SSG are present in a HPMC:SSG weight ratio between 9:1 and 1:3.

2. The excipient composition according to claim 1, wherein 0.25 g of said composition in 100 ml deionized water after 24 hours at 25° C., when subjected to centrifugation at 6080 G at 25° C. for 15 minutes, exhibits a sedimentation volume of greater than 60 ml.

3. A slow or extended release tablet formulation comprising the excipient composition according to claim 1 and one or more active ingredients.

4. The tablet according to claim 3, wherein said SSG and HPMC are present together in an amount of 10-60 wt %, based on total weight of the tablet.

5. A method of preparing a slow or extended release formulation, comprising blending the excipient composition according to claim 1 with one or more active ingredients.

6. The sedimentation volume of SSG according to claim 1 is greater than 90 ml.

7. The tablet according to claim 3, wherein the one or more active ingredient is selected from the group consisting of: vitamins, minerals, proteins, peptides, enzymes, nutraceuticals, pharmaceuticals, microorganisms and flavors.

8. The excipient composition according to claim 1, wherein the sodium starch glycolate has a degree of substitution in a range of 0.22-0.32.

9. The excipient composition according to claim 2, wherein the sedimentation volume is greater than 80 ml.

10. The excipient composition according to claim 1, wherein the sodium starch glycolate is prepared from potato starch.

11. The excipient composition according to claim 1, wherein the sodium starch glycolate is pre-gelatinized.

12. The excipient composition according to claim 1, wherein the sodium starch glycolate has a molecular weight in a range between 100 kDa-50,000 kDa.

13. The excipient composition according to claim 1, wherein the HPMC and SSG are present in a HPMC:SSG weight ratio between 7:1 to 1:2.

14. The excipient composition according to claim 1, wherein the HPMC and SSG are present in a HPMC:SSG weight ratio between 4:1 to 1:3.

15. The excipient composition according to claim 1, wherein the HPMC and SSG are present in a HPMC:SSG weight ratio between 1:1 to 1:3.

16. The tablet according to claim 3, wherein said SSG and HPMC are present together in an amount of 30-50 wt %, based on total weight of the tablet.

* * * * *